United States Patent
Richard et al.

(10) Patent No.: US 8,616,206 B2
(45) Date of Patent: Dec. 31, 2013

(54) METHOD AND APPARATUS FOR TREATING APNEA/HYPOPNEA

(75) Inventors: Ron Richard, Temecula, CA (US);
Steven Paul Farrugia, Lugarno (AU);
Philip Rodney Kwok, Chatswood (AU);
David Mulcahy, Castle Hill (AU)

(73) Assignee: ResMed Limited, Bella Vista (AU)

( * ) Notice: Subject to any disclaimer, the term of this patent is extended or adjusted under 35 U.S.C. 154(b) by 974 days.

(21) Appl. No.: 12/440,445

(22) PCT Filed: Sep. 6, 2007

(86) PCT No.: PCT/AU2007/001326
§ 371 (c)(1),
(2), (4) Date: Dec. 14, 2009

(87) PCT Pub. No.: WO2008/028248
PCT Pub. Date: Mar. 13, 2008

(65) Prior Publication Data
US 2010/0089396 A1      Apr. 15, 2010

Related U.S. Application Data

(60) Provisional application No. 60/842,995, filed on Sep. 8, 2006.

(51) Int. Cl.
*A61M 16/00* (2006.01)
(52) U.S. Cl.
USPC ............ 128/204.23; 128/204.21; 128/204.18; 128/200.24
(58) Field of Classification Search
USPC ............. 128/200.24, 204.18, 204.21, 204.23, 128/204.26
See application file for complete search history.

(56) References Cited

U.S. PATENT DOCUMENTS

| | | | |
|---|---|---|---|
| 5,245,995 A | | 9/1993 | Sullivan et al. |
| 5,458,137 A | * | 10/1995 | Axe et al. ................. 128/204.23 |
| 5,704,345 A | | 1/1998 | Berthon-Jones |
| 6,085,747 A | * | 7/2000 | Axe et al. ................. 128/204.23 |
| 6,363,933 B1 | | 4/2002 | Berthon-Jones |

(Continued)

FOREIGN PATENT DOCUMENTS

| | | |
|---|---|---|
| EP | 934723 | 9/2004 |
| WO | WO 2005/077447 | 8/2005 |

OTHER PUBLICATIONS

International Search Report for PCT/AU2007/001326, mailed Feb. 14, 2008.
Written Opinion for PCT/AU2007/001326, mailed Feb. 14, 2008.

*Primary Examiner* — Annette Dixon
(74) *Attorney, Agent, or Firm* — Nixon & Vanderhye, PC

(57) ABSTRACT

Methods and/or apparatuses for treating sleep-disordered breathing (SDB) are provided. In particular, systems and/or methods are provided which may temporarily boost the pressure of a supply of breathable gas provided by an AutoSet device for the treatment of hypopnea. In certain example embodiments, a supply of breathable is provided to patients to treat apneas and/or hypopneas. The presence and/or absence of apneas and/or hypopneas are detected (e.g. by monitoring the Apnea-Hypopnea Index). When hypopnea events are detected, the pressure of the supply of breathable gas temporarily is increased above the Pcrit and/or CPAP levels, at least during patient inspiration. When the hypopnea events are normalized, the pressure is reduced. In certain example embodiments, the pressure will not be increased when a non-hypopnea event is detected at the same time as a hypopnea event.

45 Claims, 3 Drawing Sheets

(56) References Cited

U.S. PATENT DOCUMENTS

| | | | |
|---|---|---|---|
| 6,367,474 B1 | 4/2002 | Berthon-Jones et al. | |
| 6,398,739 B1 | 6/2002 | Sullivan et al. | |
| 6,502,572 B1 | 1/2003 | Berthon-Jones et al. | |
| 6,532,960 B1 | 3/2003 | Yurko | |
| 6,635,021 B1 | 10/2003 | Sullivan et al. | |
| 6,675,797 B1 | 1/2004 | Berthon-Jones | |
| 6,770,037 B2 | 8/2004 | Sullivan et al. | |
| 6,817,361 B2 | 11/2004 | Berthon-Jones et al. | |
| 6,988,498 B2 | 1/2006 | Berthon-Jones et al. | |
| 7,004,908 B2 | 2/2006 | Sullivan et al. | |
| 2004/0016433 A1 | 1/2004 | Estes et al. | |
| 2004/0123866 A1* | 7/2004 | Berthon-Jones | 128/204.23 |
| 2005/0217674 A1* | 10/2005 | Burton et al. | 128/204.23 |

* cited by examiner

METHOD AND APPARATUS FOR TREATING APNEA/HYPOPNEA

CROSS-REFERENCE TO RELATED APPLICATION

This application claims the benefit PCT Application No. PCT/AU2007/001326, filed on Sep. 6, 2007, which is based on U.S. application Ser. No. 60/842,995, the entire contents of each of which are incorporated herein by reference.

FIELD OF THE INVENTION

The present invention relates to methods and/or apparatuses for treating sleep-disordered breathing (SDB). More particularly, the present invention relates to systems and/or methods that may temporarily boost the pressure of a supply of breathable gas provided by an AutoSet device for the treatment of hypopneas. In certain example embodiments, the pressure may increase a small amount above Pcrit and/or CPAP levels, at least during patient inspiration.

BACKGROUND OF THE INVENTION

Obstructive Sleep Apnea (OSA) and other dangerous sleep-disordered breathing (SDB) conditions affect thousands worldwide. For example, patients suffering from SDB may exhibit breathing conditions commonly referred to as apneas and/or hypopneas. Apneas are periods of time during which breathing stops or is markedly reduced. Apneas usually are measured during sleep over a given time period. Hypopneas are decreases in breathing that are not as severe as apneas. Like apneas, hypopneas usually disrupt the level of sleep. More particularly, hypopneas are a result of decreased airflow by 30-50% for at least 10 seconds, and are sometimes associated with a $SpO_2$ desaturation of 4% or greater. Hypoventilation may be associated with non-obstructive alveolar etiology, neuromuscle disease, and chest wall deformity; it also can be related to obesity and congenital central diseases. Typically, patients suspected of suffering from an SDB register with a certified sleep laboratory where sleep technicians fit patients with numerous data collectors and monitor their sleep activity over a given period.

Information relating to apneas and/or hypopneas can be monitored and processed. For example, an apnea index (AI) can estimate the severity of apnea. AI is calculated by dividing the number of apneas by the number of hours of sleep. The greater the AI, the more severe the apnea. Similarly, a hypopnea index (HI) can be calculated by dividing the number of hypopneas by the number of hours of sleep. Clinical examiners also can calculate and track an Apnea-Hypopnea Index (AHI). AHI is an index of severity that combines apneas and hypopneas. Combining apnea and hypopnea information gives an overall severity of sleep apnea including sleep disruptions and desaturations (e.g. a low level of oxygen in the blood). AHI, like AI and HI, is calculated by dividing the number of apneas and hypopneas by the number of hours of sleep. The following table provides exemplary AHI ranges and their corresponding levels of severity. It will be appreciated that the following tables are provided by way of example and without limitation, and that it may be possible to classify the level of severity using other AHI ranges.

| AHI | Level of Severity |
| --- | --- |
| 0-5 | Normal |
| 5-15 | Mild apnea |
| 15-30 | Moderate apnea |
| 30 or more | Severe |

Numerous techniques have emerged for treating and/or normalizing apneas, including, for example, introducing positive airway pressure to the patient. This technique pneumatically splints the airway open and reduces the number of apneic events. One example of such techniques makes use of Continuous Positive Airway Pressure (CPAP) devices, which continuously provide pressurized air or other breathable gas to the entrance of a patient's airways via a patient interface (e.g. a mask) at a pressure elevated above atmospheric pressure, typically in the range 3-20 cm $H_2O$.

FIG. 1 is a positive airway pressure generator in the prior art. In FIG. 1, PAP device 10 delivers a supply of pressurized, breathable gas to patient 12. The pressurized breathable gas is provided from PAP device 10 to patient 12 via flexible tube 14. Flexible tube 14 terminates with mask 16, which may, for example, be fitted for the nose patient 12. An operator, sleep clinician, or similar person may use controls 18 to specify treatment parameters such as, for example, pressure thresholds, treatment duration, type of information to monitor, etc. Processor 20 interprets these commands and instructs motor 22 to provide the supply of pressurized, breathable gas to patient 12.

Sensor 24 connected to flexible tube 14 may monitor treatment and/or event data such as, for example, presence and/or absence of apneas and/or hypopneas, patient response, etc. This information may be sent from sensor 24 to processor 20. Processor 20 may use this information, for example, to adjust the supply of pressurized, breathable gas, log treatment and/or event data, calculate information (e.g. AI, HI, AHI, etc.), etc. Commercial products corresponding to these and similar techniques include CPAP with expiratory pressure relief (EPR), AutoSet, VPAP (with and without a rate setting, which relates to the adjustable respiratory rate or breaths per minute setting), and ADAPT SV, all of which are available from ResMed. More particularly, bilevel devices such as VPAP III available from ResMed and BiPAP REMstar Pro available from Respironics, deliver a higher pressure during inspiration (IPAP), and a lower pressure during expiration (EPAP). Providing different pressures in synchrony with a patients breathing patterns are thought to provide increased comfort.

Positive airway pressure devices (e.g. those functioning in CPAP mode) can treat basic obstructive apneas and offset some hypopneas. Indeed, some commercial devices may offset some hypopneas during the course of apnea treatment. For example, ResMed's AutoSet algorithm provides a minimum set pressure (for example approximately 4 cm $H_2O$) and then detects respiratory events such as apneas, snoring, and flow limitation or flattening, etc. In response to detecting such an event, the pressure is increased at a predetermined rate depending upon the magnitude and type of event that has occurred. When events are not detected, the pressure slowly decreases at a set rate until it reaches the minimum set pressure level. Thus, the pressure is controlled based on respiratory events. This algorithm continuously provides the lowest possible pressure to prevent respiratory events. It will be appreciated that the pressure may change with each patient, based on, for example, body weight, sleep position, sleep stage, drug/alcohol intake, etc. Unlike ResMed's AutoSet algorithm, the Respironics AutoSet algorithm uses the Pcrit model to continuously calculate and adjust the supply of pressurized breathing gas to deliver the gas at Pcrit. Pcrit, or critical closing pressure, is one measure of upper airway collapsibility. Pcrit is based on the idea of modeling the upper airway as a simple collapsible tube. According to this model, Pcrit is the level of nasal pressure below which the upper airway collapses. One advantage of this model is that it gives a global measure of upper airway collapsibility that includes both the structural and neuromuscular factors that determine upper airway collapsibility. It will be appreciated that Pcrit may change with each patient, based on, for example, body weight, sleep position, sleep stage, drug/alcohol intake, etc. Although such AutoSet devices may detect hypopneas, they do not currently adjust the pressure in response to hypopnea events. Furthermore, because a hypopnea is difficult if not impossible to detect unless it is above the Pcrit level, it is similarly important to treat hypopneas above the Pcrit level.

Patients suffering from SDB may experience a combination of apneas and hypopneas. The timing of these conditions and events may vary with, for example, sleep stage, sleep position, weight loss/gain, intake of alcohol and/or medications that may depress the respiratory drive of the patient, etc. Some or all of these variables may be accounted for by enabling a device to measure and deliver varying levels of positive airway pressure to the patient. Although these techniques may reduce patients' apneic events, such treatment techniques have little effect in treating hypopneas. For example, this is because hypopneas tend only to respond to pressures above Pcrit, and some PAP devices only provide pressure levels up to Pcrit.

Thus, it will be appreciated that a need has developed in the art to overcome one or more of these and other disadvantages.

SUMMARY OF THE INVENTION

In certain example embodiments, a method of treating a patient with sleep-disordered breathing is provided. Such methods may include providing a supply of pressurized breathable gas at a treatment pressure, with the treatment pressure being substantially constant during patient inspiration and patient expiration. A first signal may be generated when a hypopnea event is detected. The pressure of the supply of pressurized breathable gas may be increased to a boosted pressure during patient inspiration in response to the first signal to normalize the hypopnea event. When the hypopnea event is normalized, the supply of pressurized breathable gas may be provided to the patient at the substantially constant treatment pressure.

In certain other example embodiments, a method of treating a patient with sleep-disordered breathing. Such methods may comprise providing a supply of pressurized breathable gas at a selectable treatment pressure according to a first treatment mode, wherein the first treatment mode provides a constant treatment pressure during patient inspiration and patient expiration. A first signal may be generated when an obstructive event is detected. The treatment pressure of the supply of pressurized breathable gas may be adjusted to treat the patient for the obstructive event in response to the first signal. A second signal may be generated when a hypopnea event is detected. A supply of pressurized breathable gas may be provided according to a second treatment mode to normalize the hypopnea in response to the second signal, wherein the second treatment mode provides an increased pressure during patient inspiration compared to the pressure provided during patient expiration. When the hypopnea event is normalized, providing a supply of pressurized breathable gas according to the first treatment mode.

Certain example embodiments provide a system for delivering therapeutic treatment pressure to a patient suffering from sleep-disordered breathing. Such systems may include a controllable flow generator operable to generate a supply of pressurized breathable gas to be delivered to the patient at a treatment pressure, with the treatment pressure being substantially constant during patient inspiration and patient expiration. A sensor may be operable to generate a signal related to the presence and/or absence of a hypopnea event. A processor may be operable to control the controllable flow generator, and may be further operable to determine whether a hypopnea event is occurring based at least in part on the signal. A pressure boost circuit responsive to the signal may be operable to instruct the controllable flow generator to increase pressure of the supply of pressurized breathable gas to a boosted pressure during patient inspiration when the signal corresponds to the occurrence of a hypopnea event until the hypopnea event is normalized.

Certain example embodiments provide a system for delivering therapeutic treatment pressure to a patient suffering from sleep-disordered breathing. Such systems may comprise a controllable flow generator operable to generate a supply of pressurized breathable gas to be delivered to the patient at a treatment pressure, with the treatment pressure being substantially constant during patient inspiration and patient expiration. A sensor may be operable to generate a first signal related to the presence and/or absence of a hypopnea event and a second signal related to the presence and/or absence of an obstructive event. A processor may be operable to control the controllable flow generator, and may be further operable to determine whether a hypopnea event is occurring based at least in part on the first signal and to determine whether an obstructive event is occurring based at least in part on the second signal. A pressure boost circuit responsive to the first signal may be operable to instruct the controllable flow generator to increase pressure of the supply of pressurized breathable gas to a boosted pressure during patient inspiration when the first signal corresponds to the occurrence of a hypopnea event until the hypopnea event is normalized.

Still other example embodiments relate to a PAP device for treating a patient suffering from sleep-disordered breathing. Such PAP devices may comprise a controllable flow generator operable to generate a supply of pressurized breathable gas to be delivered to the patient. A processor may be configured to operate in a first mode for treating an obstructive event, and may be further configured to operate in a second mode for treating a non-obstructive event. The first mode may include causing the controllable flow generator to provide the supply of pressurized breathable gas at a first treatment pressure. The second Mode may include causing the controllable flow generator to provide the supply of pressurized breathable gas at a second treatment pressure until the non-obstructive event is normalized, with the second treatment pressure at least during patient inspiration being higher than the first treatment pressure.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

DETAILED DESCRIPTION OF ILLUSTRATED EMBODIMENTS 1.0 Example Systems with Pressure Boost Circuit Referring now to the drawings in which like reference numerals indicate like parts throughout the several views, FIG. 2 is an illustrative positive airway pressure generator capable of providing a pressure boost in accordance with one example embodiment. FIG. 2 is like FIG. 1 in that it shows PAP device 10', which delivers via flexible tube 14 a supply of pressurized, breathable gas to patient 12, who is fitted with mask 16. Also similar to FIG. 1, sensor 24, which is connected to flexible tube 14, may monitor treatment and/or event data such as, for example, presence and/or absence of apneas, patient response, etc. This information may be sent from sensor 24 to processor 20'. Processor 20' may use this information, for example, to adjust the supply of pressurized, breathable gas, log treatment and/or event data, calculate information (e.g. AI, HI, AHI, etc.), etc. It will be appreciated that the device of FIG. 2 may function according to ResMed's AutoSet algorithm or as a CPAP device until a hypopnea is detected. Thus, a continuous pressure may be provided throughout a breath (e.g. substantially the same pressure may be provided during both inspiration and expiration).

1.1 Activating the Pressure Boost Circuit

Figure 1:
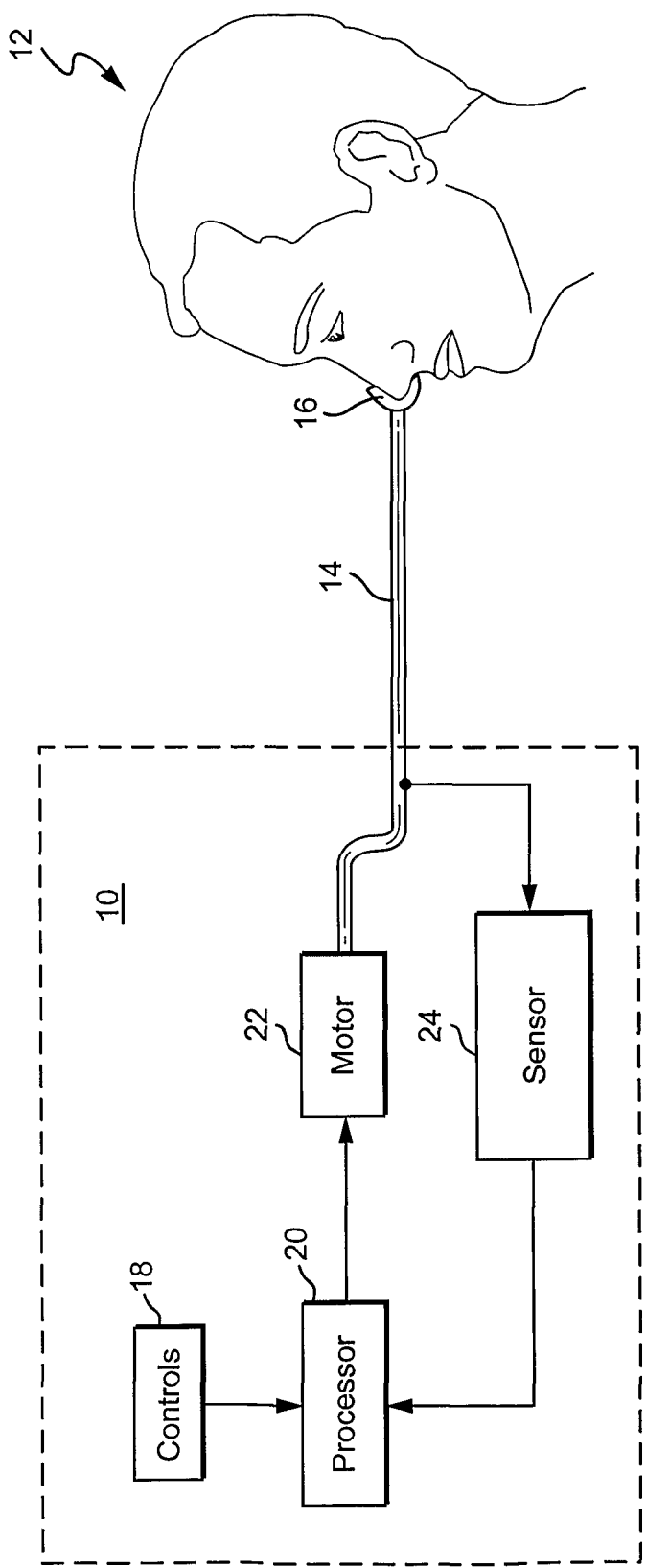
FIG. 1 is a positive airway pressure generator in the prior art.
Figure 2:
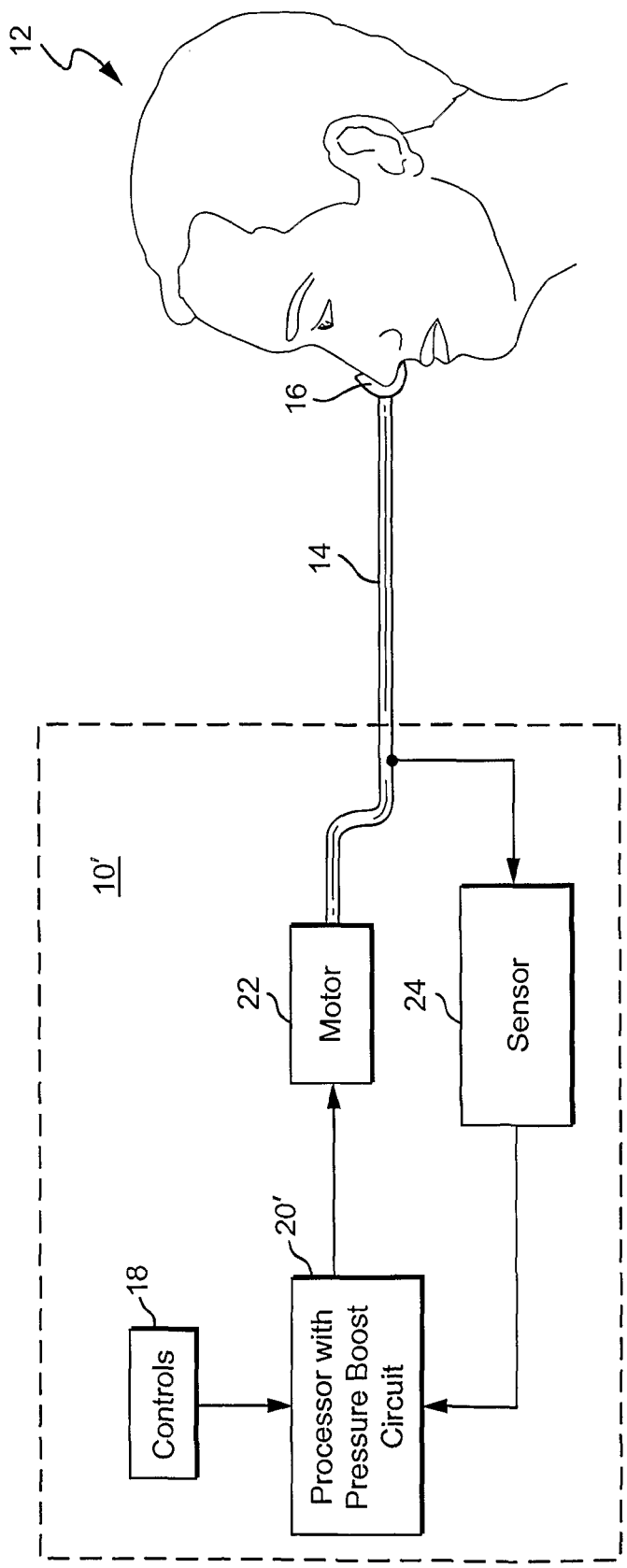
FIG. 2 is an illustrative positive airway pressure generator capable of providing a pressure boost in accordance with one example embodiment; and, FIG. 3 is an illustrative flowchart showing a method of treating apneas and/or hypopneas in accordance with one example embodiment.

In certain example embodiments, processor 20' may contain a pressure boost circuit. It will be appreciated that the pressure boost circuit may be implemented as hardware, software, firmware, a combination therebetween, etc. It also will be appreciated that while the pressure boost circuit may be integrated into processor 20', it also may be implemented as a separate element operably connected to processor 20' depending on the particular embodiment. The pressure boost circuit may interpret data from processor 20', such as, for example, AI, HI, AHI, etc. Based on this and/or other data, the processor and/or pressure boost circuit may determine that a hypopnea event is occurring.

If a hypopnea event is occurring, the pressure boost circuit may become activated, increasing the pressure of the breathable gas supplied to patient 12. The pressure may be increased, for example, above the pressure level for CPAP therapy, above the Pcrit level, etc. If the pressure level for CPAP therapy (with or without the boost) is less than Pcrit, the hypopnea most likely would not be normalized because of the limited range associated with the pressure boost. In a preferred embodiment, the pressure will increase a small amount (e.g. approximately 2 cm $H_2O$) during inspiration when a hypopnea is detected. However, it will be appreciated that in certain example embodiments, the amount of the pressure increase may vary (e.g. less than 2 cm $H_2O$ or more than 2 cm $H_2O$) and/or the pressure boost may occur at a different time (e.g. during expiration). Preferably, the pressure boost circuit may only become activated when a hypopnea occurs without another SDB-related event (e.g. apnea) also occurring at the same time. It may be possible to continue boosting the pressure in small increments if the hypopnea is not normalized. However, it will be appreciated that there is a practical limit to the pressures that can be provided. For example, it is preferable to limit the pressure boost to approximately 3 cm $H_2O$. It will be appreciated that if pressure boosts above this level are required, the patient most likely should be reassessed by the sleep clinician and may need to be switched to a bilevel device for treatment. In these ways, the pressure boost may provide a higher pressure for inspiration than expiration in a similar manner to a VPAP device, except the difference between IPAP and EPAP is more limited (e.g. up to approximately 3 cm $H_2O$). It will be appreciated that this concept is similar to EPR treatment, except reversed in that the pressure level provided during inspiration is increased rather than the pressure level provided during expiration being decreased.

1.2 Deactivating the Pressure Boost Circuit

When processor 20' and/or the pressure boost circuit determines that the hypopnea is normalized, the pressure boost circuit will become deactivated. Thus, the supply of breathable gas may be delivered to the patient at the pre-boost pressure. Normalization may be detected based on, for example, an AHI value, whether the airflow is re-established to values correlated with a patient exhibiting normal tidal volumes/minute ventilation, treated vs. untreated HI values, etc. Preferably, the device will revert to the AutoSet mode to deliver a substantially constant pressure during inspiration and expiration. Thus, certain example embodiments may be thought of as placing the device in a limited VPAP type mode to assist in overcoming a hypopnea and then returning to an AutoSet mode once the hypopnea is normalized. Of course, it will be appreciated that the pressure boost upon inspiration to treat hypopneas also may be provided with a standard CPAP device.

2.0 Example Methods for Boosting Pressure

Figure 3:
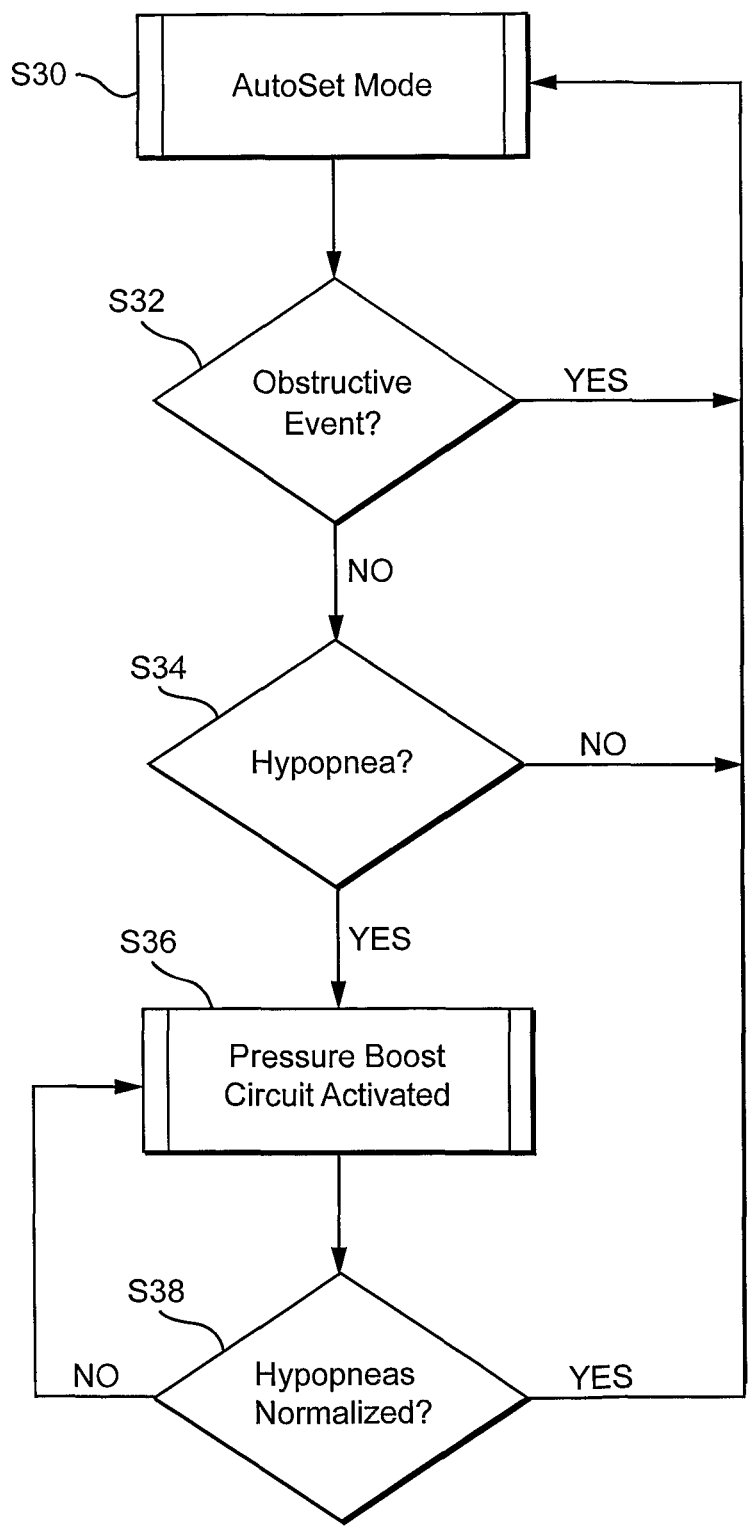

FIG. 3 is an illustrative flowchart showing a method of treating apneas and/or hypopneas in accordance with one example embodiment. The process begins with step S30, where a device operates according to an AutoSet Mode. Example AutoSet devices are disclosed in U.S. Pat. Nos. 6,367,474; 6,502,572; 6,817,361; 6,988,498; 6,363,933; 5,704,345; 6,675,797; 5,245,995; 6,398,739; 6,635,021; 6,770,037; and 7,004,908, each of which is incorporated herein by reference. Generally, AutoSet devices measure one or more parameters of the patient and set the pressure level based on the measured parameter(s). For CPAP and AutoSet devices, the pressure of the breathable gas generally is the same for expiration and inspiration. Thus, for CPAP and AutoSet devices, the pressure generally is constant and continuous. Step S32 determines whether an obstructive event (e.g. an apnea event) is occurring. An obstructive event is a cessation of airflow in the presence of an ongoing respiratory effort being made by the patient. If an obstructive event is occurring, the process returns to step S30, and the device continues to function in normal AutoSet Mode.

If an obstructive event is not taking place, step S34 determines whether a hypopnea is occurring. If there is no hypopnea occurring, the process returns to step S30, and the device continues to function in normal AutoSet Mode. If, however, a hypopnea is occurring in step S34, the pressure boost circuit is activated in step S36. As noted above, the pressure boost circuit may increase pressure a small amount (e.g. approximately 2 cm $H_2O$) above Pcrit and/or CPAP levels. After the pressure boost is activated, step S38 will determine whether the hypopnea has been normalized. If the hypopnea has been normalized, the pressure boost is removed, the process returns to step S30, and the device returns to normal AutoSet Mode.

If, however, the hypopnea is not normalized, the pressure boost remains active until the step S38 determines that the hypopnea has been normalized/offset.

Introducing devices capable of treating both apneas and hypopneas may be advantageous for dealers and patients. For example, combining functions may eliminate the need to stock a multiplicity of different devices, thus reducing overhead costs. Patients suffering from both apneas and hypopneas may realize improved comfort and efficacy over current technologies as more and more of their symptoms may be treated. For example, patients may receive better overall therapy because products according to the embodiments described herein may be capable of treating both apneas and hypopneas. Also, combining apnea and hypopnea treatment functions may ease the prescription and diagnosis process for patients who exhibit apneas and intermittent hypopneas. These patients may receive varying treatments without further diagnoses and/or the purchase of additional treatment devices.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments.

Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in nonmedical applications.

What is claimed is:

1. A method of treating a patient with sleep-disordered breathing, the method comprising:
   providing a supply of pressurized breathable gas at a treatment pressure, the treatment pressure being substantially constant during patient inspiration and patient expiration;
   generating a first signal when a hypopnea event is detected;
   increasing the pressure of the supply of pressurized breathable gas to a boosted pressure during patient inspiration in response to the first signal to normalize the hypopnea event; and,
   when the hypopnea event is normalized, providing the supply of pressurized breathable gas to the patient at the substantially constant treatment pressure.

2. The method of claim 1, further comprising:
   generating a second signal when an obstructive event is detected; and,
   adjusting the substantially constant treatment pressure in response to the second signal.

3. The method of claim 2, wherein the pressure of the supply of pressurized breathable gas is increased to the boosted pressure only when an obstructive event is not detected.

4. The method of claim 2, wherein the substantially constant pressure is adjusted to be the greater of a minimum set pressure and a lowest possible pressure to treat the obstructive event.

5. The method of claim 1, wherein the boosted pressure is a pressure above a predetermined threshold pressure.

6. The method of claim 5, wherein the threshold pressure is Pcrit.

7. The method of claim 5, wherein the threshold pressure is the treatment pressure.

8. The method of claim 5, wherein the boosted pressure is approximately 1-3 cm $H_2O$ above the threshold pressure.

9. The method of claim 1, wherein the hypopnea event and/or the hypopnea normalization is detected based at least in part on an Apnea-Hypopnea Index.

10. The method of claim 1, wherein the supply of pressurized breathable gas is provided by a CPAP device.

11. The method of claim 1, wherein the supply of pressurized breathable gas is provided by a device configured to monitor at least one parameter of the patient and provide the pressure of the breathable gas based on the at least one parameter.

12. The method of claim 1, wherein the pressure of the breathable gas is in the range of approximately 3-20 cm $H_2O$.

13. The method of claim 1, wherein the boosted pressure is less than approximately 3 cm $H_2O$ above a predetermined threshold level.

14. The method of claim 13, wherein the threshold level is a Pcrit level associated with the patient.

15. A method of treating a patient with sleep-disordered breathing, the method comprising:
   providing a supply of pressurized breathable gas at a selectable treatment pressure according to a first treatment mode, wherein the first treatment mode provides a constant treatment pressure during patient inspiration and patient expiration;
   generating a first signal when an obstructive event is detected;
   adjusting the treatment pressure of the supply of pressurized breathable gas to treat the patient for the obstructive event in response to the first signal;
   generating a second signal when a hypopnea event is detected;
   providing a supply of pressurized breathable gas according to a second treatment mode to normalize the hypopnea in response to the second signal, wherein the second treatment mode provides an increased pressure during patient inspiration compared to the pressure provided during patient expiration; and,
   when the hypopnea event is normalized, providing a supply of pressurized breathable gas according to the first treatment mode.

16. The method of claim 15, wherein the pressure provided during patient expiration in the second treatment mode is the same as the treatment pressure provided during the first treatment mode.

17. The method of claim 15, wherein the supply of pressurized gas is provided according to the second treatment mode only when an obstructive event is not detected.

18. A system for delivering therapeutic treatment pressure to a patient suffering from sleep-disordered breathing, comprising:
   a controllable flow generator operable to generate a supply of pressurized breathable gas to be delivered to the patient at a treatment pressure, the treatment pressure being substantially constant during patient inspiration and patient expiration;

a sensor operable to generate a signal related to the presence and/or absence of a hypopnea event;

a processor operable to control the controllable flow generator, and further operable to determine whether a hypopnea event is occurring based at least in part on the signal; and, a pressure boost circuit responsive to the signal operable to instruct the controllable flow generator to increase pressure of the supply of pressurized breathable gas to a boosted pressure during patient inspiration when the signal corresponds to the occurrence of a hypopnea event until the hypopnea event is normalized.

19. The system of claim 18, wherein the sensor is further operable to generate a second signal related to the presence and/or absence of an obstructive event, and wherein the processor is further operable to adjust the substantially constant treatment pressure based on a determination as to whether an obstructive event is occurring, the determination as to whether an obstructive event is occurring being based at least in part on the second signal.

20. The system of claim 19, wherein the pressure boost circuit instructs the controllable flow generator to increase the pressure of the supply of pressurized breathable gas when a hypopnea is occurring and no obstructive event is occurring.

21. The method of claim 19, wherein the substantially constant pressure is adjusted to be the greater of a minimum set pressure and a lowest possible pressure to treat the obstructive event.

22. The system of claim 18, wherein the boosted pressure is a pressure above a predetermined threshold pressure.

23. The system of claim 22, wherein the threshold pressure is Pcrit.

24. The system of claim 22, wherein the threshold pressure is the treatment pressure.

25. The system of claim 22, wherein the boosted pressure is approximately 1-3 cm $H_2O$ above the threshold pressure.

26. The system of claim 22, wherein the hypopnea event and/or the hypopnea event normalization is detected based at least in part on an Apnea-Hypopnea Index.

27. The system of claim 22, wherein the flow generator is a CPAP device.

28. The system of claim 22, wherein the treatment pressure is in the range of approximately 3-20 cm $H_2O$.

29. The system of claim 22, wherein the boosted pressure is less than approximately 3 cm $H_2O$ above a predetermined threshold level.

30. The system of claim 29, wherein the predetermined threshold level is a Pcrit level associated with the patient.

31. A system for delivering therapeutic treatment pressure to a patient suffering from sleep-disordered breathing, comprising:

a controllable flow generator operable to generate a supply of pressurized breathable gas to be delivered to the patient at a treatment pressure, the treatment pressure being substantially constant during patient inspiration and patient expiration;

a sensor operable to generate a first signal related to the presence and/or absence of a hypopnea event and a second signal related to the presence and/or absence of an obstructive event;

a processor operable to control the controllable flow generator, and further operable to determine whether a hypopnea event is occurring based at least in part on the first signal and to determine whether an obstructive event is occurring based at least in part on the second signal; and, a pressure boost circuit responsive to the first signal operable to instruct the controllable flow generator to increase pressure of the supply of pressurized breathable gas to a boosted pressure during patient inspiration when the first signal corresponds to the occurrence of a hypopnea event until the hypopnea event is normalized.

32. The system of claim 31, wherein the pressure boost circuit instructs the controllable flow generator to increase the pressure of the supply of pressurized breathable gas when a hypopnea is occurring and no obstructive event is occurring.

33. A PAP device for treating a patient suffering from sleep-disordered breathing, comprising:

a controllable flow generator operable to generate a supply of pressurized breathable gas to be delivered to the patient; and, a processor configured to operate in a first mode for treating an obstructive event, and further configured to operate in a second mode for treating a non-obstructive event;

wherein the first mode includes causing the controllable flow generator to provide the supply of pressurized breathable gas at a first treatment pressure, and wherein the second mode includes causing the controllable flow generator to provide the supply of pressurized breathable gas at a second treatment pressure until the non-obstructive event is normalized, the second treatment pressure at least during patient inspiration being higher than the first treatment pressure.

34. The PAP device of claim 33, wherein the second treatment pressure is a pressure above Pcrit.

35. The PAP device of claim 34, wherein the second treatment pressure is approximately 1-3 cm $H_2O$ above Pcrit.

36. The PAP device of claim 33, wherein the processor operates in the second mode only when the processor is not operating in the first mode.

37. The PAP device of claim 33, wherein the processor is operable to switch between the first and mode the second mode in response to an AHI of the patient.

38. The PAP device of claim 33, wherein the flow generator is a CPAP device.

39. The PAP device of claim 38, wherein the first treatment pressure is substantially constant during patient inspiration and patient expiration at least when the processor operates in the first mode.

40. The PAP device of claim 33, wherein the pressure of the breathable gas is in the range of approximately 3-20 cm $H_2O$.

41. The PAP device of claim 33, wherein the second treatment pressure is less than approximately 3 cm $H_2O$ above a predetermined threshold level.

42. The PAP device of claim 33, wherein the threshold level is a Pcrit level associated with the patient.

43. The PAP device of claim 33, wherein the flow generator is a bilevel device.

44. The PAP device of claim 43, wherein the flow generator is operable to provide the supply of pressurized breathable gas at a first inhalation pressure during patient inhalation and a second expiration pressure during patient expiration when the processor operates in the first mode, the first pressure being different from the second pressure.

45. The PAP device of claim 44, wherein the flow generator is operable to increase the first pressure and/or the second pressure when the processor operates in the second mode.

* * * * *